(12) United States Patent  
Pond

(10) Patent No.: US 6,419,485 B1
(45) Date of Patent: Jul. 16, 2002

(54) MULTIPLE SOLUTION DENTAL IRRIGATOR

(76) Inventor: Gary J. Pond, 2816 N. Main St., Racine, WI (US) 53402

( * ) Notice: Subject to any disclaimer, the term of this patent is extended or adjusted under 35 U.S.C. 154(b) by 0 days.

(21) Appl. No.: 09/468,524

(22) Filed: Dec. 21, 1999

(51) Int. Cl.[7] .............................. A61C 17/02; A61C 3/02
(52) U.S. Cl. ............................................ 433/80; 433/88
(58) Field of Search ................................ 433/82, 80, 88

(56) References Cited

U.S. PATENT DOCUMENTS

| | | |
|---|---|---|
| 611,136 A | 9/1898 | Mason |
| 1,672,114 A | 6/1928 | Crow |
| RE21,187 E | 8/1939 | Hooper |
| 2,214,230 A | 9/1940 | Freeburg |
| 2,557,222 A | 6/1951 | Goode |
| 2,711,586 A | 6/1955 | Groves ........................ 433/95 |
| 2,756,740 A | 7/1956 | Deane ........................ 604/249 |
| 2,812,765 A | 11/1957 | Tofflemire |
| 2,929,510 A | 3/1960 | Penn |
| 2,985,285 A | 5/1961 | Riddle |
| 3,164,153 A | 1/1965 | Zorzi |
| 3,208,145 A | 9/1965 | Turner |
| 3,593,423 A | 7/1971 | Jones et al. ................... 433/80 |
| 3,624,907 A | 12/1971 | Brass et al. |
| 3,640,304 A | 2/1972 | Fox et al. ...................... 433/80 |
| 3,645,497 A | 2/1972 | Nyboer ........................ 433/95 |
| 3,718,973 A | 3/1973 | Slater et al. |
| 3,727,310 A | 4/1973 | Baker |
| 3,757,421 A | 9/1973 | Kraft |
| 3,971,375 A | 7/1976 | Hill ............................. 433/98 |
| 4,106,198 A | 8/1978 | Childress |
| 4,215,476 A | 8/1980 | Armstrong .................. 433/80 |
| 4,227,878 A | 10/1980 | Lohn ........................... 433/80 |
| 4,253,831 A | 3/1981 | Eaton, II ...................... 433/91 |
| 4,340,365 A | 7/1982 | Pisanu ......................... 433/80 |
| 4,353,694 A | 10/1982 | Pelerin ......................... 433/77 |
| 4,397,640 A | 8/1983 | Haug et al. ................... 604/33 |
| 4,526,573 A | 7/1985 | Lester et al. .................. 604/33 |
| 4,552,531 A | 11/1985 | Martin ........................ 433/147 |
| 4,578,055 A | 3/1986 | Fischer ......................... 604/2 |
| 4,680,026 A | 7/1987 | Weightman et al. .......... 604/33 |
| 4,797,098 A | 1/1989 | Kawata ........................ 433/98 |
| D302,586 S | 8/1989 | Zogg et al. |
| 4,872,837 A | 10/1989 | Issalene et al. ............... 433/29 |
| 5,044,953 A | 9/1991 | Sullivan ...................... 433/92 |
| 5,052,927 A | 10/1991 | Discko, Jr. ................... 433/90 |
| 5,061,180 A | 10/1991 | Wiele .......................... 433/91 |
| 5,087,198 A | 2/1992 | Castellini .................... 433/80 |
| 5,171,146 A | 12/1992 | Guerci ......................... 433/81 |
| 5,199,604 A | 4/1993 | Palmer et al. ................ 433/80 |
| 5,204,004 A | 4/1993 | Johnston et al. ............. 433/80 |
| 5,236,356 A | 8/1993 | Davis et al. |
| 5,289,919 A | 3/1994 | Fischer ........................ 206/571 |
| 5,378,149 A | 1/1995 | Stropko ....................... 433/80 |
| 5,378,150 A | 1/1995 | Harrel ......................... 433/91 |
| 5,419,772 A | 5/1995 | Teitz et al. .................. 604/141 |
| 5,468,148 A | 11/1995 | Ricks .......................... 433/80 |
| 5,474,450 A | 12/1995 | Chronister ................... 433/80 |
| 5,526,841 A | 6/1996 | Detsch et al. ................. 137/15 |
| 5,554,026 A | 9/1996 | Van Hale ..................... 433/82 |
| 5,556,279 A | * 9/1996 | Wolf et al. ................... 433/88 |
| 5,593,304 A | * 1/1997 | Ram ............................ 433/82 |
| 5,658,144 A | 8/1997 | Tinder et al. ................ 433/80 |
| 5,716,210 A | 2/1998 | Novak ......................... 433/82 |
| 5,772,433 A | 6/1998 | Esrock ........................ 433/80 |
| 5,837,204 A | * 11/1998 | Prevost et al. ............... 433/80 |
| 5,876,201 A | 3/1999 | Wilson et al. ................ 433/80 |
| 5,899,692 A | 5/1999 | Davis et al. .................. 433/80 |
| 5,927,977 A | 7/1999 | Sale et al. |
| 5,947,729 A | 9/1999 | Bell ............................ 433/98 |

\* cited by examiner

Primary Examiner—Cary E. O'Connor
(74) Attorney, Agent, or Firm—Ryan Kromholz & Manion, S.C.

(57) ABSTRACT

A fluid dispensing assembly that may be used interchangeably to supply fluid for use in dental instrumentation including irrigation, application, and aeration for treating a patient's mouth. The fluid dispensing assembly includes a fluid supply system that conveys fluid by pressurized air, and also includes a handpiece to allow flow between the fluid supply system and the patient's mouth.

17 Claims, 4 Drawing Sheets

MULTIPLE SOLUTION DENTAL IRRIGATOR

BACKGROUND OF THE INVENTION

1. Field of the Invention

This invention relates to systems and methods and methods for systems for providing fluid to a hand tool and associated supply lines.

2. Description of Related Art

As a patient sits in a dental chair in a dentist's office, the dentist or a hygienist ordinarily cleans the patient's teeth with a variety of picks and brushes. Next, the dentist or a hygienist uses a hand held tool to supply rinse water, a variety of other medicament fluids from supply lines to a patient's mouth. U.S. patent parent application Ser. No. 09/054,277, filed on Apr. 2, 1998, and commonly assigned to the assignee hereof, discloses such a dental handpiece, and more particularly a handpiece that may be used interchangeably as an irrigator, an aerator, an applicator or as an evacuator for treating a patient's mouth.

The air lines in such a handpiece are commonly shared at the air supply with other air operated hand tools used in a dental office at the operators disposal. Therefore, the air supply pressure in each dental office is unique to that office because some dentists may operate more or less air tools from the same air supply.

Some dental handpieces are able to, supply a plurality of fluids to a patient's mouth. One such example is U.S. Pat. No. 4,215,476 to Armstrong. However, such handpieces often involve complex solenoid valves and more expensive electrical controls to toggle between fluid sources. Further, such handpieces often physically toggle fluid sources at the fluid source, controlled by a toggling at the handpiece. It is has been found that toggling fluid sources at the handpiece itself, rather than at the more remote fluid source, requires a much lesser volume of fluid to be purged through the lines after fluid changes. Toggling at the handpiece itself results in less fluid wasted, and reduces the risks that fluids may interact within a common fluid line and lead to undesirable chemical reactions.

SUMMARY OF THE INVENTION

To overcome the above-identified concerns, the present invention provides a very inexpensive apparatus and method for a fluid supply system that is capable of supplying multiple fluids to a patients mouth.

The various components may be made using conventional molding and extrusion techniques from inexpensive materials, both relatively rigid and also very flexible when needed or required.

A fluid dispensing assembly for dispensing a plurality of fluids is disclosed, the fluid dispensing assembly comprising a handpiece, a fluid discharge disposed on the handpiece, and a control mechanism disposed on the handpiece, the control mechanism controlling whether fluid dispenses from the fluid discharge. A plurality of fluid inlets are disposed on the handpiece, as well as a manual switch disposed on the handpiece, operable to toggle between fluid inlets. The fluid dispensing assembly further comprises a fluid supply system, a plurality of fluid outlet lines, the fluid outlet lines communicatively coupled between the fluid supply system and the fluid inlets.

The fluid supply system comprises a plurality of reservoirs, a volume of fluid contained within each reservoir, and a reservoir head detachably coupled to each reservoir. A source of pressurized air is used to force fluid from each reservoir to the fluid inlet on the handpiece. An air pressure regulator can be used to adjust air pressure, and thus adjust fluid flow from the handpiece.

A method for supplying fluid from two sources to a handpiece is also disclosed, the method comprising: attaching a first fluid containing reservoir to a first reservoir head, coupling a first fluid outlet line between the first fluid containing reservoir and the handpiece, attaching a second fluid containing reservoir to a second reservoir head, coupling a second fluid outlet line between the second fluid containing reservoir and the handpiece, supplying pressurized air to the first and second fluid containing reservoirs, the pressurized air forcing the fluid from the first and second fluid containing reservoirs through the first and second fluid outlet lines to the handpiece, toggling a manual switch disposed on the handpiece, the manual switch operable to select between the first and second fluid outlet lines, and actuating a control mechanism to allow the fluid to pass from the selected fluid outlet line through the handpiece. If it is desired to purge the handpiece of fluid from the fluid outlet line previously used, the operator can toggle between fluid sources, and then an initial purge volume flow through the handpiece

DETAILED DESCRIPTION

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

It is to be noted that like elements of the drawings are designated by like reference numbering.

The term fluid, as used herein, shall be defined as a gas including air, a liquid, a substance which flows, or a substance which differs from a solid in that it can offer no permanent resistance to change of shape. It shall further include mixtures of gases, mixtures of liquids, and mixtures of gases and liquids.

Figure 1:
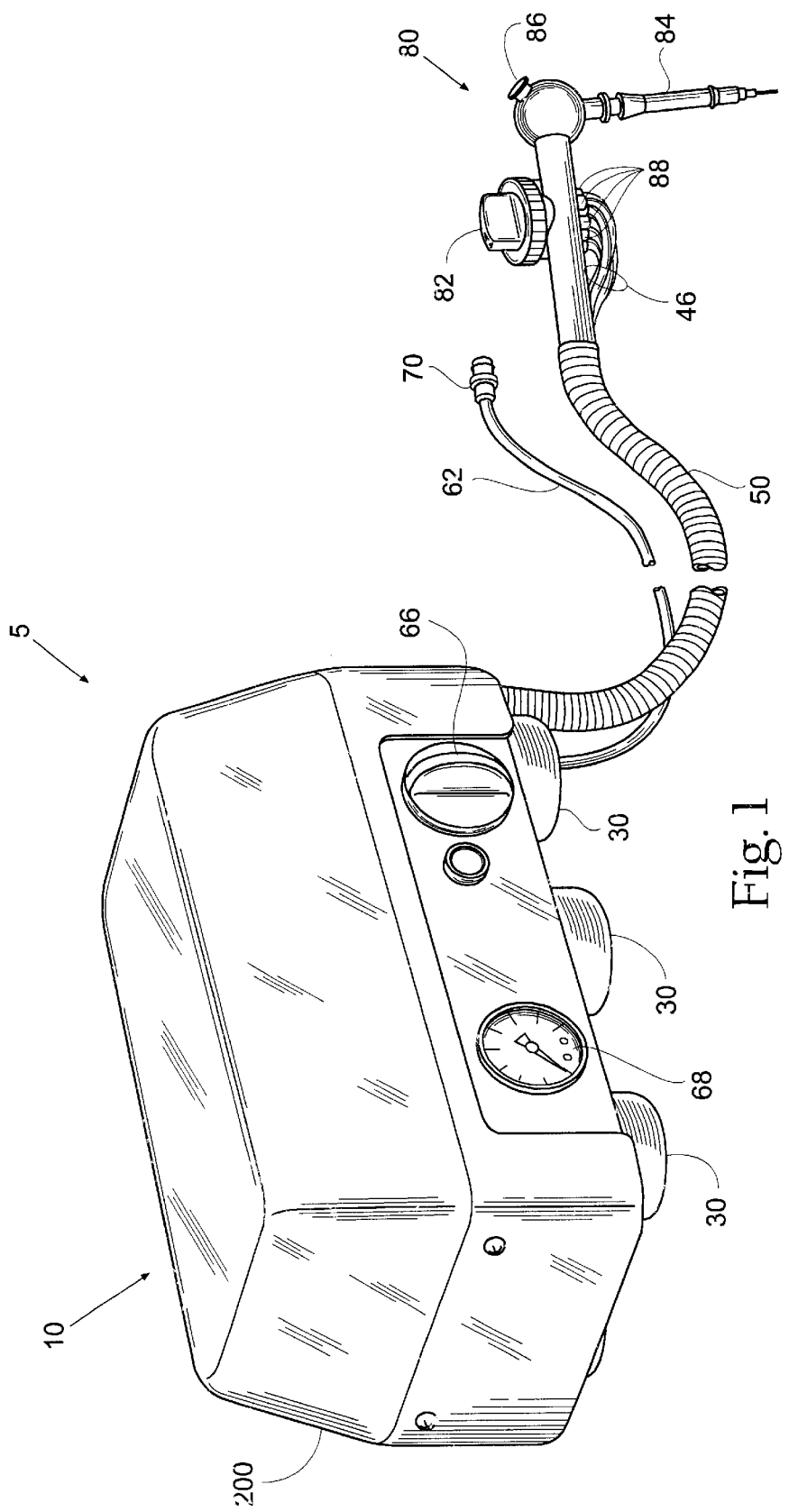
FIG. 1 is a perspective view of fluid dispensing assembly.
Figure 2:
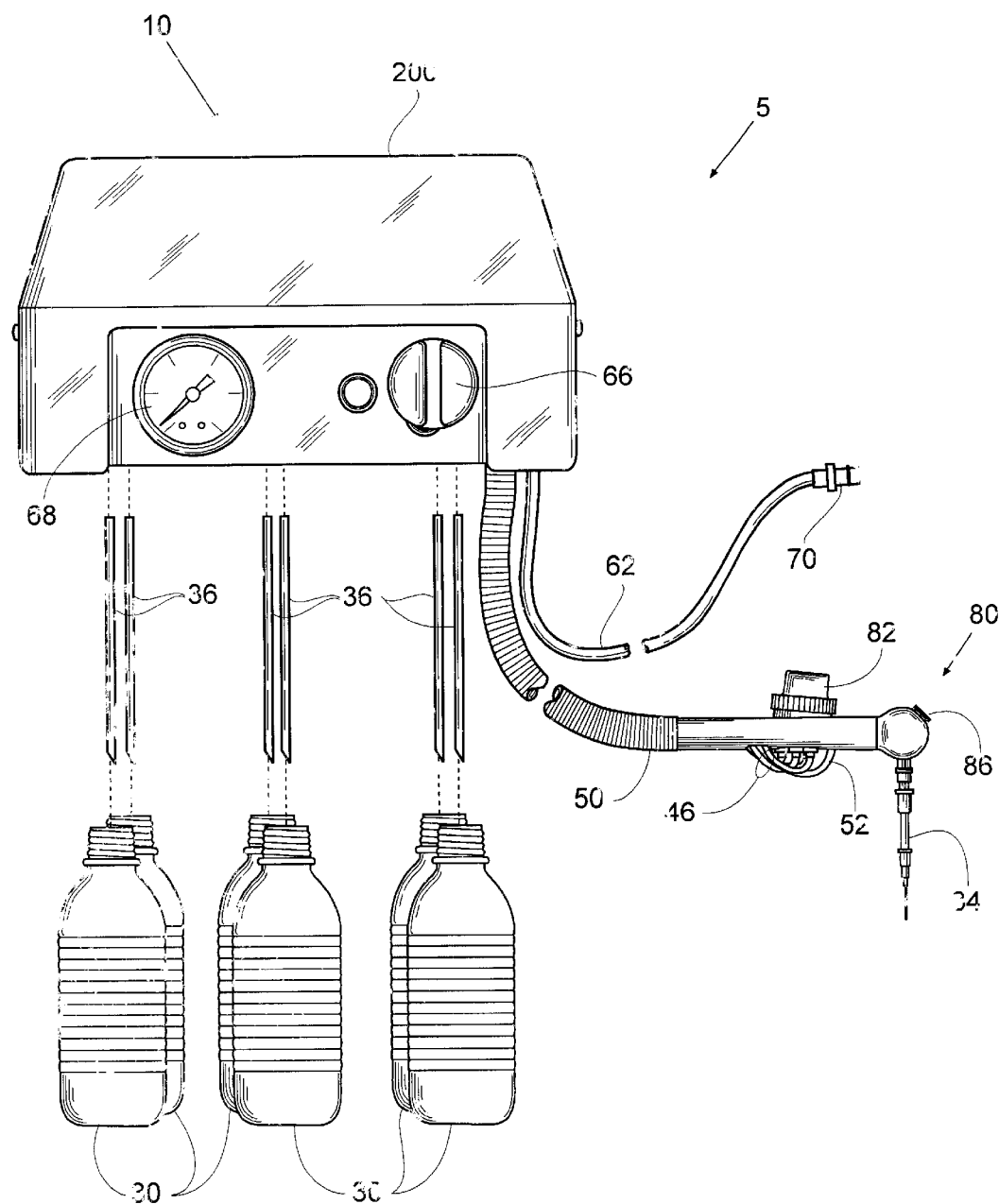
FIG. 2 is a front perspective view of a fluid dispensing assembly, with some components detached.
Figure 4:
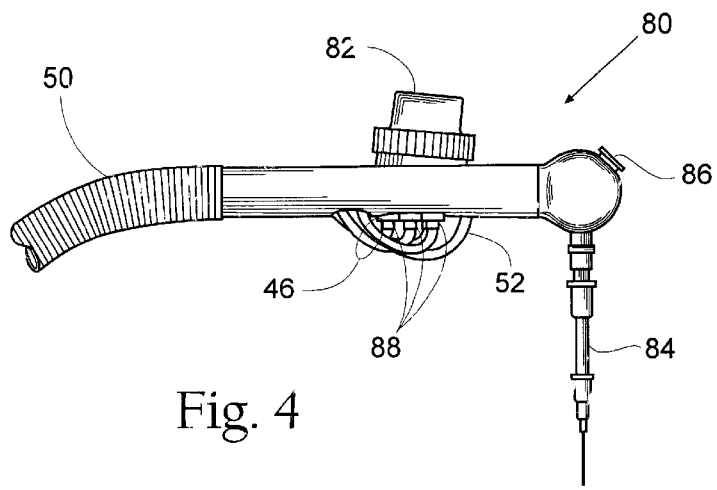
FIG. 4 is a side perspective view of a handpiece of the fluid dispensing assembly.
Figure 5:
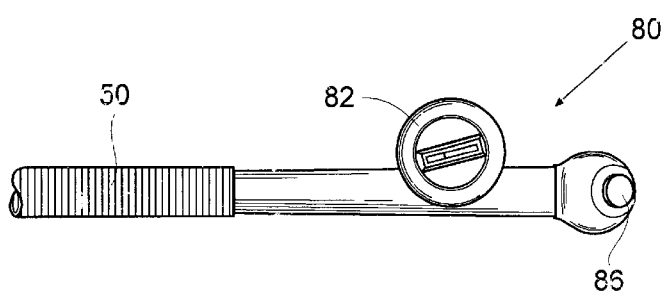
FIG. 5 is a top perspective view of the handpiece of the fluid dispensing assembly.
Figure 6:
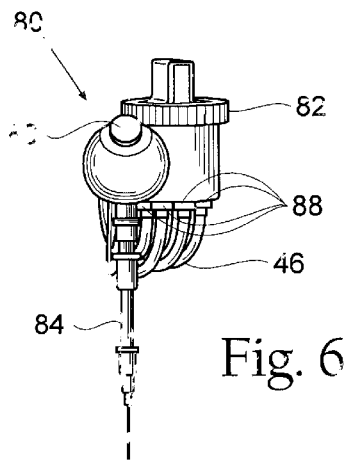
FIG. 6 is a front perspective view of the handpiece of the fluid dispensing assembly
Figure 7:
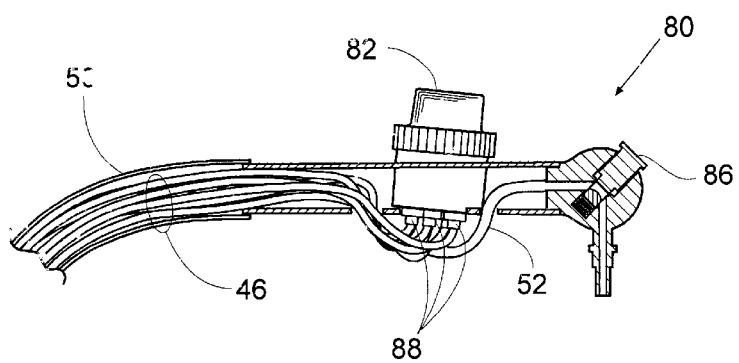
FIG. 7 is a side perspective view of the handpiece of the fluid dispensing assembly, partially in cross-section.
Figure 3:
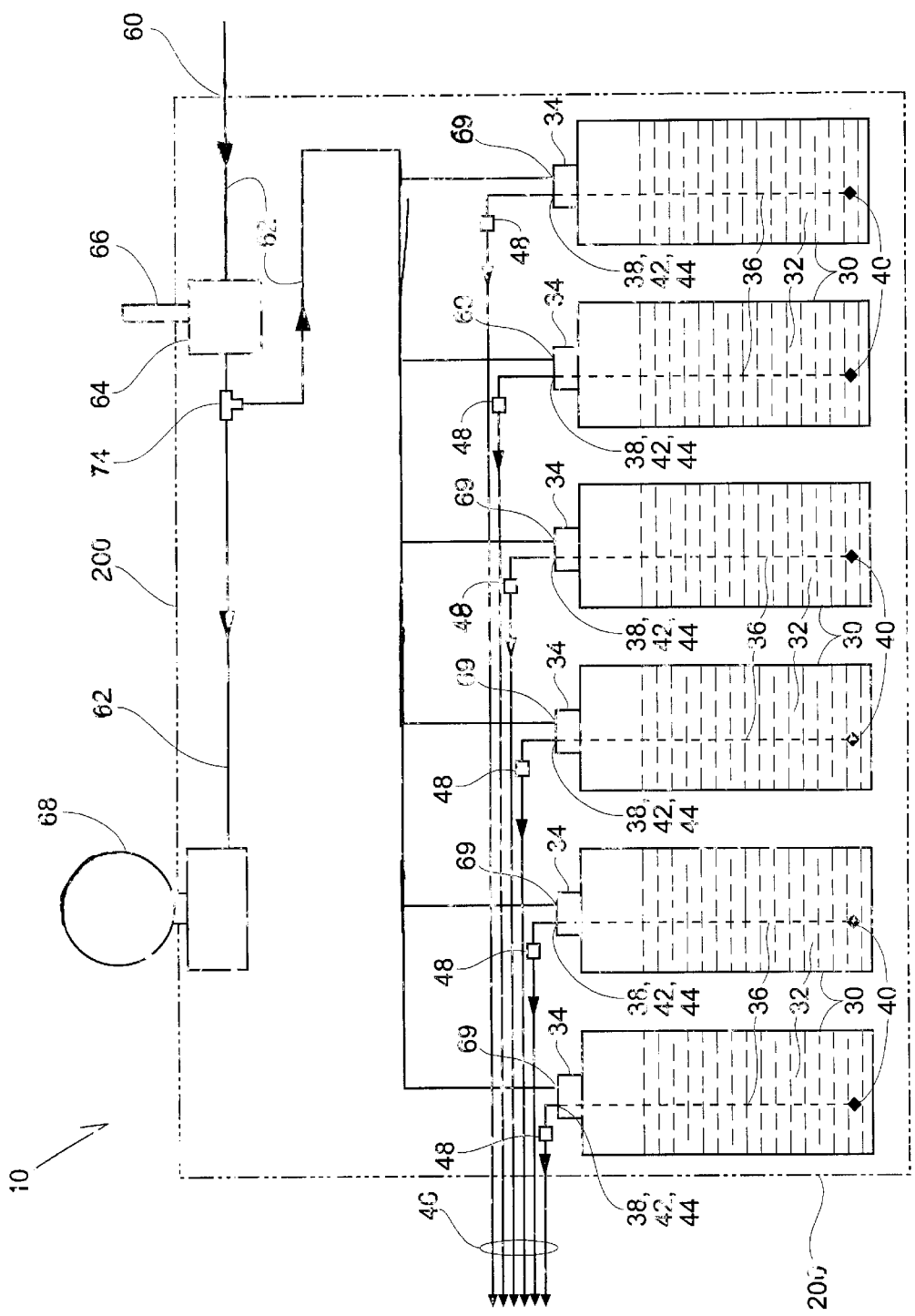
FIG. 3 is a schematic view of a fluid supply system.

Referring to FIGS. 1, 2 and 3, a fluid dispensing assembly 5 capable of supplying irrigation and aeration from a fluid supply system 10 to a dental handpiece 80 is disclosed. The fluid dispensing assembly 5 includes a reservoir 30 capable of containing fluid 32. The reservoir 30 can come in many forms, including for example a bottle, a canister, a dual-compartment bottle or canister; and can range greatly in size. Preferably, however, the reservoir 30 is an inexpensive clear plastic bottle with a threaded opening, similar to a common water bottle with the cap removed. Reservoirs of this type are readily available from a variety of sources and manufacturers, and are most commonly available in a 10–20 fluid ounce capacity size. The clear bottle allows for a determination of the amount of fluid 32 remaining in the reservoir 30, and a reservoir of this type is capable of withstanding internal pressure, though typically the resilience to pressure for this type of reservoir is limited to approximately 50 pounds per square inch (psi). Although a stronger reservoir is capable of use with the fluid supply system, such as a high density polyethylene reservoir, the polyethylene terephthalate elastomer (PETE) construction common to plastic soda and water bottles provides sufficient rigidity, is easily available, and is inexpensive.

Referring now to FIGS. 2 and 3, the reservoir 30 is detachably coupled to a reservoir head 34 (hidden from view in FIG. 2). The reservoir head 34 is designed to provide the reservoir 30 with an air-tight seal capable of containing pressures up to 50 psi, but higher pressures are capable with different reservoir embodiments. Preferably, the detachable coupling is a threaded coupling, with a male thread on the reservoir 30, and the female thread on the reservoir head 34. The detachable coupling allows for quick and simple reservoir changes, should refills or different fluids be desired for use with the fluid dispensing assembly 5.

Referring to FIGS. 2 and 3, the reservoir head 34 has two fluid passageways, or two communicative conduits between the reservoir 30 and the remainder of the fluid dispensing assembly 5 and fluid supply system 10. The first communicative conduit provides a pathway to the interior of the reservoir for pressurized air or an air inlet fitting 69. The second communicative conduit is a fluid inlet fitting 42, providing a fluid passage for fluid to leave the reservoir.

A fluid draw line 36 having a proximal end 38 and a distal end 40 is coupled to the fluid inlet fitting 42 on the reservoir head at proximal end 38. The fluid draw line 36 is sized to extend at proximal end 38 from the top of the reservoir 30 to the bottom of the reservoir 30 at distal end 40 so that the fluid supply system 10 can operate until the reservoir 30 is nearly empty of fluid 32. A fluid outlet line 46 is communicatively coupled with a fluid outlet fitting 44, extending the pathway for fluid 32 leaving the reservoir 30. Of course, the fluid outlet fitting 44 and the fluid inlet fitting 42 could comprise a one-piece fluid passageway.

Preferably, the fluid outlet line 46 includes a check valve 48 coupled with the fluid outlet line 46, in order to prevent fluid 32 from flowing back into the reservoir 30. The fluid outlet line 46 terminates at the handpiece 80. If the operator desires to convey air to the patient's mouth, an empty reservoir 30 is supplied.

Alternatively, the fluid draw line 36 and the fluid outlet line 46 could be integrated into one line serving the same purpose of providing a conduit for fluid 32 to leave the reservoir 30 and retain pressure within the reservoir 30, if an air-tight fitting around the line is used as opposed to a fluid inlet fitting 42 and fluid outlet fitting 44. However, the use of both the fluid draw line 36 and the fluid outlet line 46 along with the fluid inlet fitting 42 and the fluid outlet fitting 44 is preferred, mainly because this arrangement provides a better pressure seal than a single line with an air-tight fitting around the line.

Preferably, an outlet line sheath 50 is provided between the fluid supply system 10 and the handpiece 80. The sheath is preferably flexible, allowing ease of mobility during treatment, but also rigid enough to withstand penetration and line puncture.

Because of the desirability of the fluid supply system 10 to supply sodium hypochlorite at times, used to either irrigate, debride and disinfect the mouth of a patient, or to destroy bacteria present in the dental unit water line, the components of the fluid supply system 10 that come into contact with the sodium hypochlorite are preferably constructed of material capable of withstanding the corrosive effects of the sodium hypochlorite. These components, including the check valve 48, fluid draw line 36, fluid outlet line 46, fluid inlet fitting 42, fluid outlet fitting 44, reservoir 30, reservoir head 34, and handpiece 80, are preferably constructed of sodium hypochlorite resistant material. Because sodium hypochlorite is particularly corrosive with respect to metal, non-metal components are preferred. Plastic is a preferred construction material because of its resistance to sodium hypochlorite corrosion.

Dental offices are often unique with respect to the air pressure in the air system. Dental offices operate at higher or lower pressures based on operator preference, the sizing of the air compressor, the number of components in the office using air, and the number of components in use at any one time. For this reason, the fluid supply system 10 is supplied with an air pressure regulator 64 coupled with the air supply line 62 between the air inlet 60 and the reservoir 30, as is best shown in FIG. 3. This avoids erratic and uncontrollable fluid flow from the fluid supply system 10 and ultimately the handpiece 80. Preferably, the air pressure regulator 64 is adjustable by operation of an air pressure regulator adjuster 66, giving an operator of the fluid supply system 10 the capability to alter the air pressure to provide a consistent output. One air pressure regulator that performs suitably is an AIRTROL R-920-03/35-3T 1–150 psi air pressure regulator. Most dentists prefer a setting of approximately 20–40 psi, with a setting of approximately 28 psi common.

As shown in FIGS. 1 and 3, the pressurized air is conveyed from a conventional source of pressurized air common in dental offices, through an air supply line 62 coupled with the source of pressurized air by a coupling 70. The air supply line 62 is communicatively coupled with the reservoir head 34 and leads to the aforementioned first communicative conduit at air inlet fitting 69 to supply pressurized air to the reservoir 30. The pressurized air is supplied to force fluid 32 from the reservoir 30 through a distal end 40 of the fluid draw line 36 through the fluid inlet fitting 42 and fluid outlet fitting 44 and through the fluid outlet line 46, a plurality of handpiece fluid inlets 88, and ultimately to components of the handpiece 80.

After the air supply line 62 enters the fluid supply system 10 and enters the air pressure regulator 64, the air supply line is split by a common tee-fitting 74 to split the air passage into two distinct pathways. As shown on FIG. 3, the first pathway leads to a pressure gauge 68. The second pathway for air travel leads to the reservoir 30 as previously mentioned. Preferably, the common tee fitting 74 may be used to split the air flow, although two separate air supply lines could be used with one air line directed to the reservoir 30 and the other supply line directed to the, pressure gauge 68. However, the tee fitting 74 used to split the one air supply line 62 into two pathways is preferred to minimize the number of fittings within the fluid supply system 10, and to simplify construction of the fluid supply system 10.

Still referring to FIG. 3, in one embodiment of the present invention, the fluid supply system 10 is equipped with six reservoirs 30, allowing the fluid supply system 10 to supply six different fluids 32 or a greater volume of the same fluid 32, to only one handpiece 80.

Referring to FIGS. 4–7, in order for the operator to select which fluid to use, a toggle switch 82 is provided on the handpiece 80. Pressure is maintained at each reservoir 30, allowing the operator to quickly supply the desired fluid following a toggle of the toggle switch 82, as opposed to having to wait for the air supply to re-pressurize the reservoir 30 with each alternation in fluid. This is preferable because the fluid 32 in each fluid outlet line 46 will remain pressurized at the handpiece 80.

Referring to FIG. 2, the fluid supply system 10 supplied with a housing 200, provided as a hub for simple instrumentation configuration changes, and as a hub for the fuid supply system 10 componentes. The housing 200 creates an attractive portal for quick connections and flexibility during instrtumentation, and also provides an easily accesible autside surface for regulating the air pressure with the air pressure regulator switch 66

During instrumentation, an operator can configure the fluid supply system 10 to supply different fluids 32 and finger tip controlled irrigation, aeration to a patient's mouth. Referring now to FIGS. 4–7, the dental handpiece 80 has a tip 84, preferably disposable for use between different patients. The tip 84 receives the selected fluid 32 through a discharge line 52 coupled to the manual toggle 82, and receiving fluid 32 from only the selected fluid outlet line 46. The disposable tip 84 is selectively coupled to the discharge line 52, and the disposable tip 84 is then used during instrumentation to direct the deposit of fluids or evacuation target site in a patient's mouth. Also disposed on the handpiece 80 is a control mechanism 86, for actuating between fluid discharge and no discharge. This control mechanism is preferably a simple and inexpensive trumpet valve, as is well known in the art.

In this arrangement, only the relatively small amount of fluid 32 contained within the discharge line 52 and the tip 84 need be purged between fluid alternations.

To supply fluid 32 from two different sources to the handpiece 80, the user first attaches the first fluid-containing reservoir 30 to a first reservoir head 34. Next, the user couples the first fluid outlet line 46 between the first fluid containing reservoir 32 and the handpiece 80, and attaches a second fluid containing reservoir 32 to a second reservoir head 34. Next, the user couples a second fluid outlet line 46 between the second fluid containing reservoir 30 and the handpiece 80. After supplying pressurized air to the first and second fluid containing reservoirs 30, the pressurized air forces the fluid 32 from the first and second fluid containing reservoirs 30 through the first and second fluid outlet lines 46 to the handpiece 80. The user can then toggle manual switch 82 disposed on the handpiece 80 in order to select the desired fluid. The manual switch is operable to select between the first and second fluid outlet lines 46. Next, the user actuates actuating the control mechanism 86 to allow the fluid 32 to pass under air pressure from the selected fluid outlet line 46 through the handpiece 80 and ultimately the tip 84. If it is desired to purge the handpiece 80 of fluid 32 from the fluid outlet line 46 previously used, the operator can toggle between fluid sources, and then allow an initial purge volume flow through the handpiece 80.

Accordingly, the invention comprises a fluid dispensing assembly 5 whereby the dentist can supply fluids 32 that irrigate the field of operation within a patient's mouth with fluids.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. A fluid dispensing assembly for dispensing a plurality of fluids, the fluid dispensing assembly comprising:
    a handpiece;
    a fluid discharge disposed on the handpiece;
    a control mechanism disposed on the handpiece, the control mechanism controlling whether fluid dispenses from the fluid discharge;
    a plurality of fluid inlets disposed on the handpiece; a manual switch disposed on the handpiece, the manual switch operable to toggle between fluid inlets;
    a fluid supply system including a plurality of reservoirs, a volume of fluid contained within each reservoir; a reservoir head detachably coupled to each reservoir; a source of pressurized air; an air supply line communicatively coupled between the source of pressurized air and each reservoir head, the air pressurized at a pressure capable of forcing fluid from each reservoir to the fluid inlet; and
    a plurality of fluid outlet lines the fluid outlet lines communicatively coupled between the fluid supply system and the fluid inlets.

2. A fluid dispensing assembly according to claim 1, the fluid supply system further comprising:
    an air pressure regulator coupled with the air supply line between the source of pressurized air and each reservoir head.

3. A fluid dispensing assembly according to claim 2, wherein the air pressure regulator is adjustable.

4. A fluid dispensing assembly according to claim 1, the fluid supply system further comprising:
    an air pressure gauge coupled to the air supply line.

5. A fluid dispensing assembly according to claim 1, wherein the fluid outlet lines are communicatively coupled with the reservoirs.

6. A fluid dispensing assembly according to claim 5, the fluid supply system further comprising:
    a fluid draw line contained within each reservoir, each fluid draw line communicatively coupled with one of the fluid outlet lines.

7. A fluid dispensing assembly according to claim 6, each fluid outlet line having a proximal end and a distal end, each fluid draw line having a proximal end and a distal end, the fluid supply system further comprising:
    a fluid passage disposed through each reservoir head, the fluid passage having an interior end and an exterior end;
    the proximal end of each of the fluid draw lines coupled with the interior end of one of the fluid passages, the proximal end of each of the fluid outlet lines coupled with the exterior end of one of the fluid passages, the distal end of each of the fluid outlet lines coupled to one of the fluid inlets on the handpiece.

8. A fluid dispensing assembly according to claim 7, the fluid supply system further comprising:
    a check valve coupled with each fluid outlet line.

9. A fluid dispensing assembly according to claim 1, the fluid dispensing assembly further comprising:
    a housing coupled with the fluid supply system.

10. A method for supplying fluid from two sources to a handpiece which utilizes the fluid dispensing assembly of claim 1.

11. A method for supplying fluid from two sources to a handpiece, the method comprising:
   attaching a first fluid containing reservoir to a first reservoir head;
   coupling a first fluid outlet line between the first fluid containing reservoir and the handpiece;
   attaching a second fluid containing reservoir to a second reservoir head;
   coupling a second fluid outlet line between the second fluid containing reservoir and the handpiece;
   supplying pressurized air to the first and second fluid containing reservoirs;
   the pressurized air forcing the fluid from the first and second fluid containing reservoirs through the first and second fluid outlet lines to the handpiece;
   toggling a manual switch disposed on the handpiece, the manual switch operable to select between the first and second fluid outlet lines;
   actuating a control mechanism to allow the fluid to pass from the selected fluid outlet line through the handpiece.

12. A method for supplying fluid from two sources to a handpiece according to claim 11, the method further comprising:
   preceding the step of actuating the control mechanism to allow fluid to pass from the selected fluid outlet line through the handpiece, actuating the control mechanism to purge the handpiece of the deselected fluid from the deselected fluid outlet line.

13. A method for supplying fluid from two sources to a handpiece according to claim 11, the method further comprising:
   after the step of supplying pressurized air to the first and second fluid containing reservoirs, the pressurized air forcing the fluid from the first and second fluid containing reservoirs through the first and second fluid outlet lines to the handpiece, adjusting the pressure of the pressurized air to a therapeutically effective level.

14. A fluid dispensing assembly for dispensing a plurality of fluids, the fluid dispensing assembly comprising:
   a handpiece;
   a fluid discharge disposed on the handpiece;
   a means for controlling whether fluid dispenses from the fluid discharge;
   a plurality of fluid inlets disposed on the handpiece;
   a plurality of fluid sources, wherein each fluid source is connected to one of the fluid inlets;
   a means for toggling between fluid inlets to select fluid flow from one of said fluid inlets to the handpiece.

15. A fluid dispensing assembly according to claim 14, the fluid dispensing assembly further comprising:
   a fluid source;
   a means for conveying fluid from the fluid source to the handpiece.

16. A fluid dispensing assembly according to claim 15, the means for conveying fluid from the fluid source to the handpiece comprising:
   a fluid containing reservoir;
   a means for pressurizing air in a void space in the fluid containing reservoir.

17. A fluid dispensing assembly according to claim 16, wherein the means for pressurizing air is adjustable.

* * * * *